US011571012B2

(12) United States Patent
Park et al.

(10) Patent No.: US 11,571,012 B2
(45) Date of Patent: Feb. 7, 2023

(54) STRAIN DERIVED FROM TRADITIONAL FERMENTED FOOD AND HAVING EXCELLENT ENZYME PRODUCTIVITY, AND METHOD FOR PREPARING FERMENTED CEREAL ENZYME FOOD BY USING SAME

(71) Applicant: CJ WELLCARE CORPORATION, Seoul (KR)

(72) Inventors: Min Ju Park, Suwon (KR); Ah Jin Kim, Seoul (KR); Sung Wook Han, Seoul (KR); Su Jin Heo, Bucheon (KR); Tae Joo Yang, Suwon (KR); Seung Won Park, Yongin (KR); Sang Bum Lee, Seoul (KR); Jae Ho Jang, Seoul (KR); Seong Jun Cho, Seoul (KR); Young Ho Hong, Suwon (KR); Sung Hee Park, Seoul (KR)

(73) Assignee: CJ WELLCARE CORPORATION, Seoul (KR)

( * ) Notice: Subject to any disclaimer, the term of this patent is extended or adjusted under 35 U.S.C. 154(b) by 770 days.

(21) Appl. No.: 15/770,712

(22) PCT Filed: Oct. 26, 2016

(86) PCT No.: PCT/KR2016/012109
§ 371 (c)(1),
(2) Date: Apr. 24, 2018

(87) PCT Pub. No.: WO2017/074037
PCT Pub. Date: May 4, 2017

(65) Prior Publication Data
US 2019/0098923 A1    Apr. 4, 2019

(30) Foreign Application Priority Data

Oct. 26, 2015 (KR) ........................ 10-2015-0148663

(51) Int. Cl.
| | |
|---|---|
| A23L 29/00 | (2016.01) |
| C12N 1/20 | (2006.01) |
| A23L 7/104 | (2016.01) |
| A61K 35/742 | (2015.01) |
| A61P 1/00 | (2006.01) |
| A23L 33/135 | (2016.01) |
| C12R 1/07 | (2006.01) |

(52) U.S. Cl.
CPC ............. *A23L 29/065* (2016.08); *A23L 7/104* (2016.08); *A23L 33/135* (2016.08); *A61K 35/742* (2013.01); *A61P 1/00* (2018.01); *C12N 1/20* (2013.01); *C12N 1/205* (2021.05); *C12R 2001/07* (2021.05)

(58) Field of Classification Search
CPC ...... A23L 29/065; A23L 7/104; A23L 33/135; A61K 35/747; A61K 35/742; A61P 1/00; C12N 1/20; C12N 1/205; C12R 1/07; C12R 2001/07

USPC .......................................................... 426/61
See application file for complete search history.

(56) References Cited

U.S. PATENT DOCUMENTS

| | | |
|---|---|---|
| 8,846,029 B2 | 9/2014 | Israelsen |
| 8,900,570 B2 | 12/2014 | Israelsen |
| 9,205,114 B2 | 12/2015 | Israelsen |
| 2004/0063184 A1* | 4/2004 | Grichko ................... C12P 7/06 435/161 |
| 2008/0057047 A1* | 3/2008 | Sas .......................... A61P 43/00 424/93.46 |
| 2008/0311097 A1 | 12/2008 | Israelsen |
| 2010/0303953 A1 | 12/2010 | Hamaker et al. |
| 2012/0269791 A1 | 10/2012 | Israelsen |
| 2013/0195821 A1 | 8/2013 | Israelsen |
| 2013/0209404 A1 | 8/2013 | Israelsen |
| 2015/0359836 A1 | 12/2015 | Israelsen |
| 2017/0020161 A1 | 1/2017 | Kim et al. |
| 2017/0333514 A1 | 11/2017 | Israelsen |

FOREIGN PATENT DOCUMENTS

| | | |
|---|---|---|
| CN | 101448398 A | 6/2009 |
| CN | 102533576 A | 7/2012 |
| CN | 103876155 A | 6/2014 |
| CN | 103907748 A | 7/2014 |
| CN | 104388335 A | 3/2015 |
| CN | 104877937 A | 9/2015 |
| JP | S6349049 A | 3/1988 |
| JP | 2009519238 A | 5/2009 |
| JP | 2013144712 A | 7/2013 |
| JP | 2015524277 A | 8/2015 |

(Continued)

OTHER PUBLICATIONS

NPL Woon et al. (Machine translation of KR10-2014-0053674A) (Year: 2014).*
NPL Sartori M et al. ( Food Additives and Contaminants vol. 29, No. 2 , 287-292, 2012). (Year: 2012).*
The above NPL Sartori M et al. document was retroeved from Google Scholar Search retrieved on Jul. 30, 2021. (Year: 2021).*
NPL Yeun et al. (Machine English Translation of (KR10-2015-0089321 A: Machine translation) (Year: 2015).*
Peng, et al., "Purification and Characterization of a Fibrinolytic Enzyme Produced by Bacillus Amyloliquefaciens DC-4 Screened from Douchi, a Traditional Chinese Soybean Food," Comp. Biochem. Phsiol. B Biochem Mol. Biol., 2003, vol. 134(1), pp. 45-52.

(Continued)

*Primary Examiner* — Erik Kashnikow
*Assistant Examiner* — Bhaskar Mukhopadhyay
(74) *Attorney, Agent, or Firm* — Birch, Stewart, Kolasch & Birch, LLP

(57) ABSTRACT

Disclosed are a novel strain of *Bacillus amyloliquefaciens*, a method of producing fermented grains using the strain, fermented grains produced using the strain, and a composition for thrombolysis; digestion improvement; prophylaxis, amelioration or treatment of bowel inflammation, serous membrane weakening or intestinal injury; or antioxidation, comprising the fermented grains.

26 Claims, 8 Drawing Sheets

Specification includes a Sequence Listing.

(56) References Cited

FOREIGN PATENT DOCUMENTS

| KR | 20080095652 A | 10/2008 |
|---|---|---|
| KR | 20110076332 A | 7/2011 |
| KR | 20120072919 A | 7/2012 |
| KR | 20130095127 A | 8/2013 |
| KR | 10-2014-0053674 A | 5/2014 |
| KR | 20140089046 A | 7/2014 |
| KR | 10-2015-0089321 A | 8/2015 |
| KR | 10-2015-0117184 A | 10/2015 |
| WO | 2015115790 A1 | 8/2015 |

OTHER PUBLICATIONS

Yuji Kubo et al., "Phylogenetic Analysis of Bacillus subtilis Strains Applicable to Natto (Fermented Soybean) Production", Applied and Environmental Microbiology, Sep. 2011, pp. 6463-6469, vol. 77, No. 18, American Society for Microbiology.

M. Park, "Bacillus amyloliquefaciens strain BA245 16S ribosomal RNA gene, partial sequence", Genbank Accession No. KR535604, Jul. 18, 2015.

Hyoung Churl Bae et al., "Characteristics of a-Amylase and Protease Produced from Bacillus amyloliquefacies CNL-90 Isolated from Malt Grain", Journal of Animal Science and Technology, 2012, pp. 133-139, vol. 54, No. 2, National Digital Science Library.

Dhanya Gangadharan et al., "Solid Culturing of Bacillus amyloliquefaciens for Alpha Amylase Production", Food Technol. Biotechnol., 2006, pp. 269-274, vol. 44, No. 2.

International Search Report for PCT/KR2016/012109 filed on Oct. 26, 2016.

Chinese Office Action for Appl. No. 201680062909.7 dated Feb. 19, 2021.

Li-Ma, "Research Progress of Douchi Fibrinolytic Enzyme," Food Processing, 2007, issue 5, pp. 83-86.

Wu, H., et al, "Effects of Bacillus amyloliquefaciens on the antioxidant function of Caco 22 cells," Animal Husbandry and Veterinary Medicine, 2011, vol. 43, No. 4, pp. 44-46.

Author Unknown, "The food enzyme preparation and its source list (Table C.3)", Chinese National Standard GB 2760-2014, Dec. 24, 2014, pp. 190-191 (3 pages total).

Chinese Office Action for Chinese Application No. 201680062909.7, dated Jan. 12, 2022, with English translation.

* cited by examiner

[Fig. 1a]
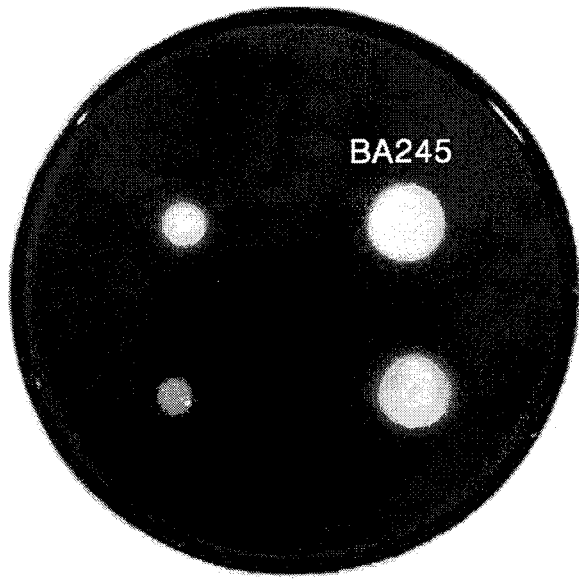
[Fig. 1b]
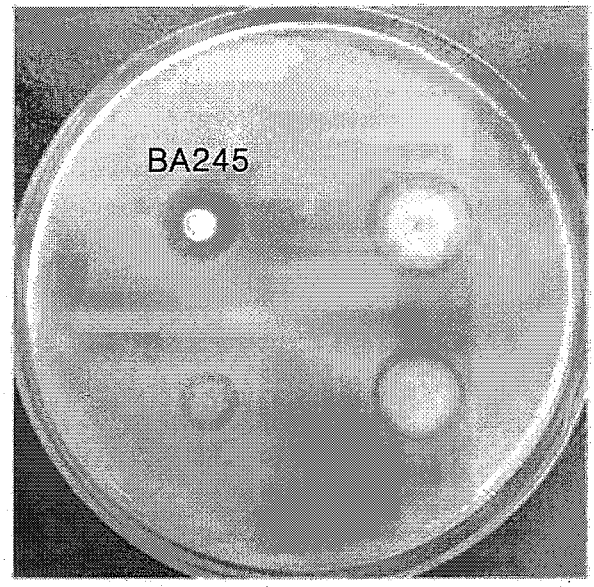

[Fig. 2]
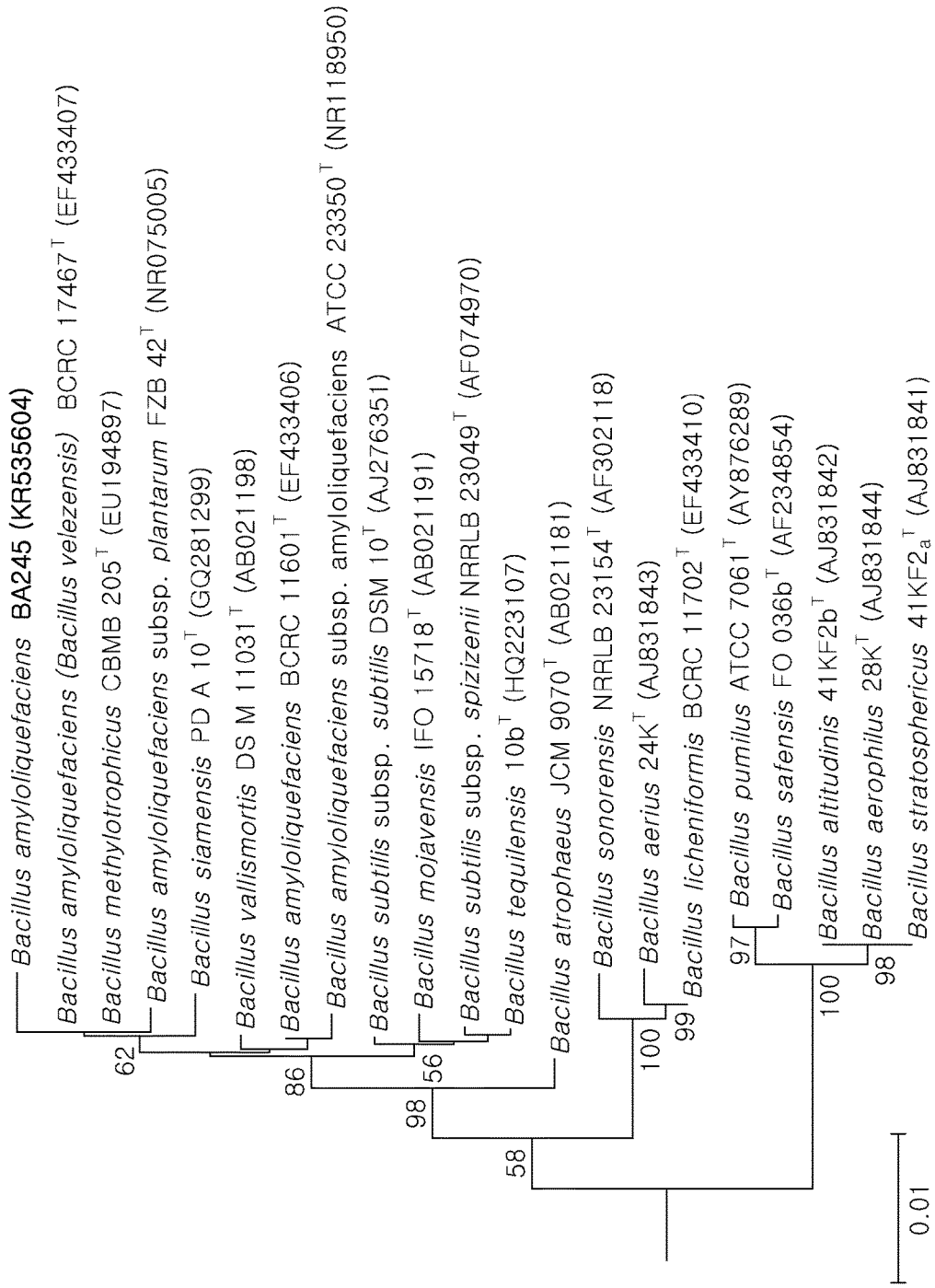

[Fig. 3]
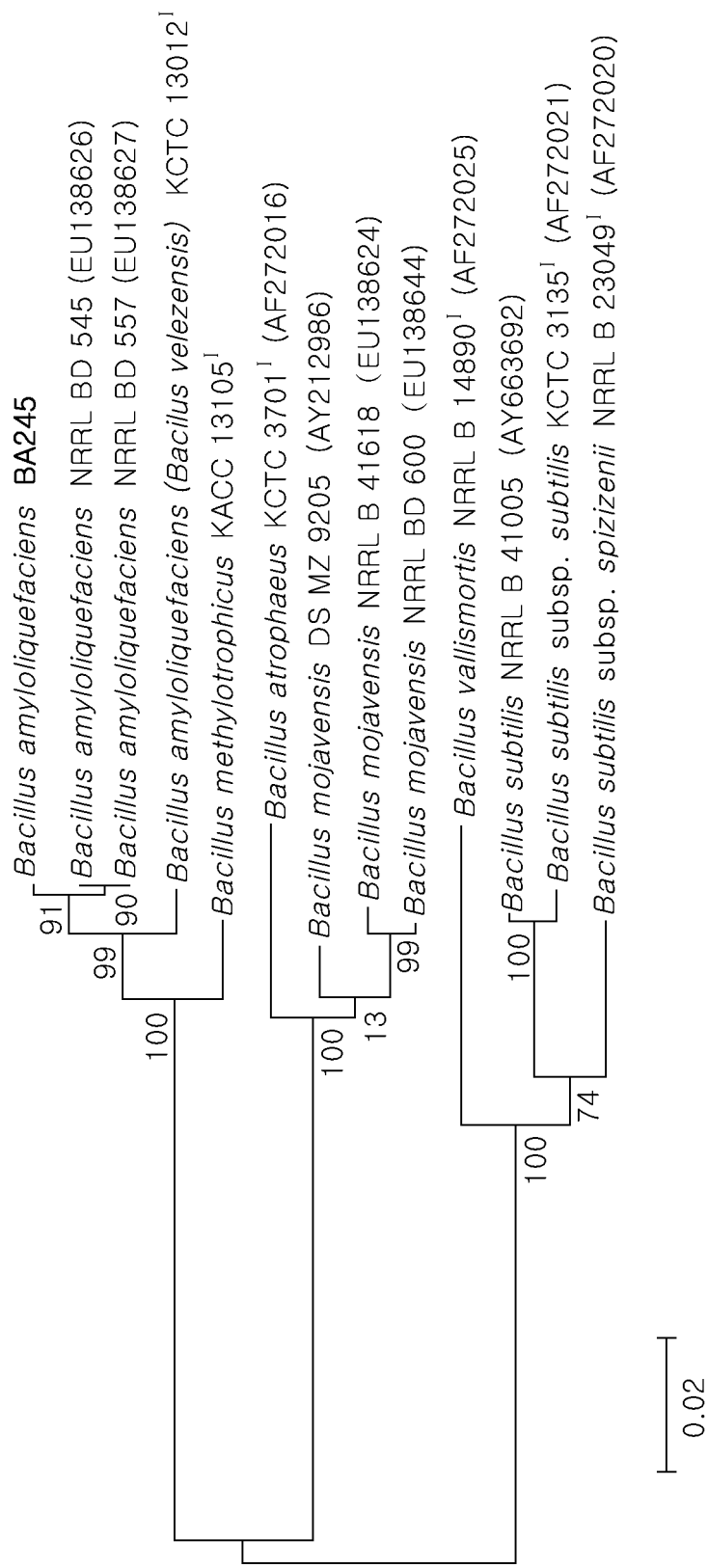

[Fig. 4]
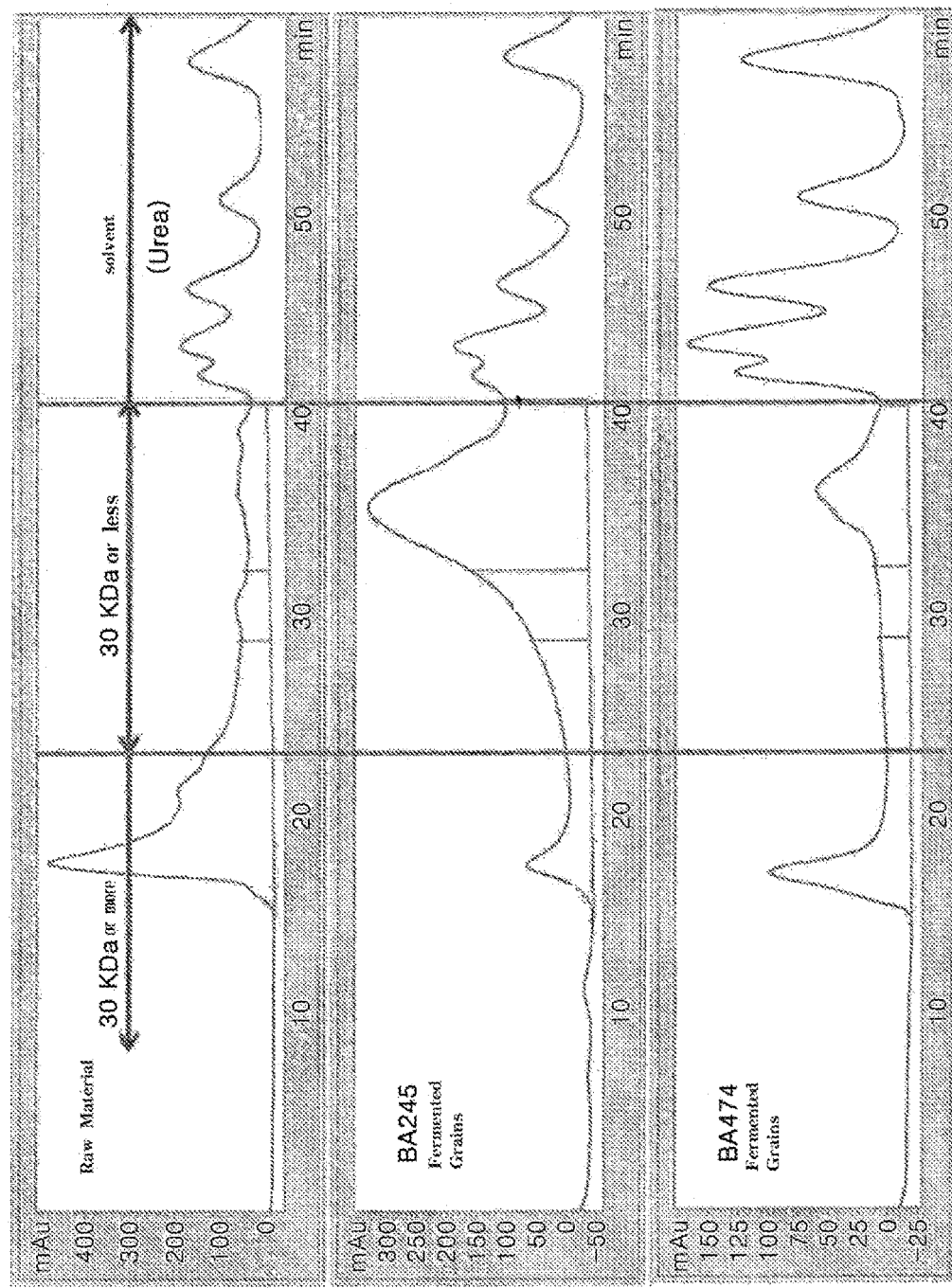

[Fig. 5]
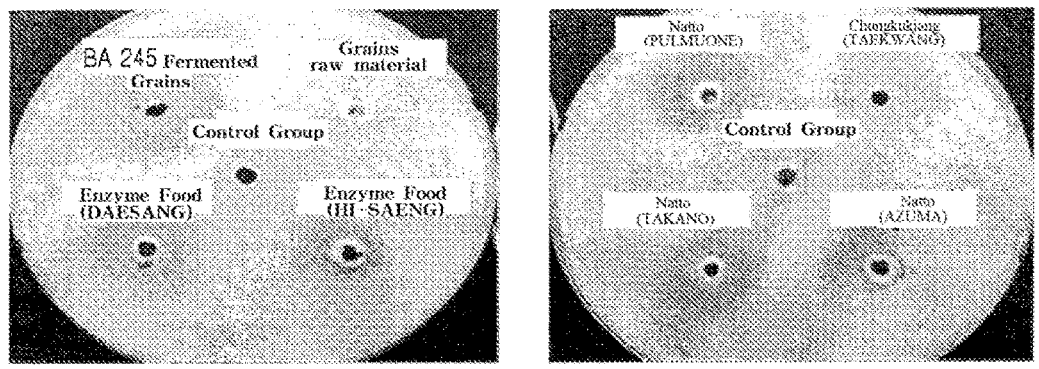
[Fig. 6]
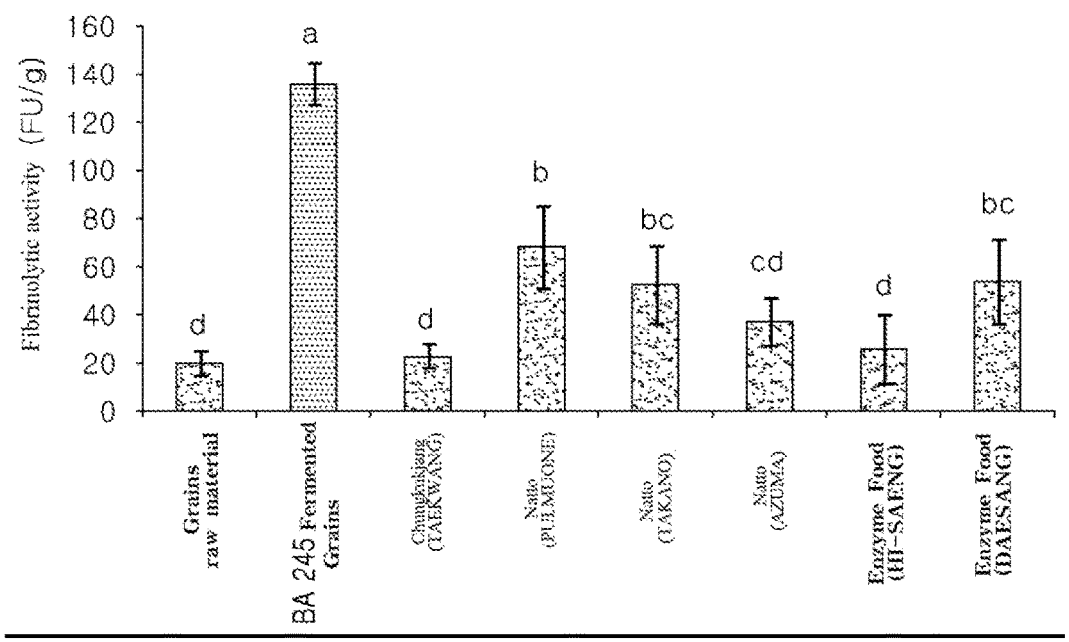

[Fig. 7]
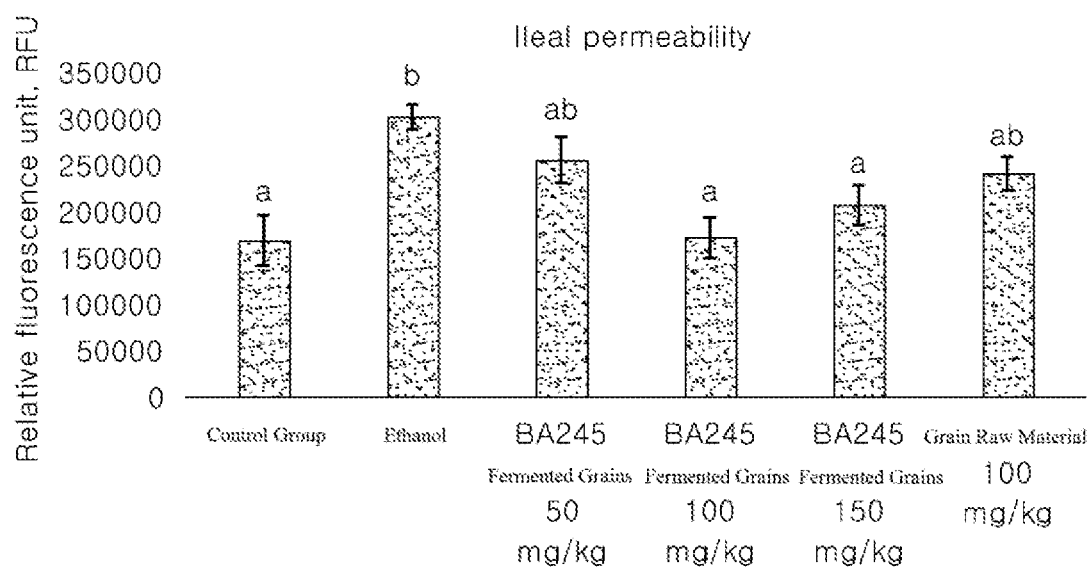

[Fig. 8]
(a)
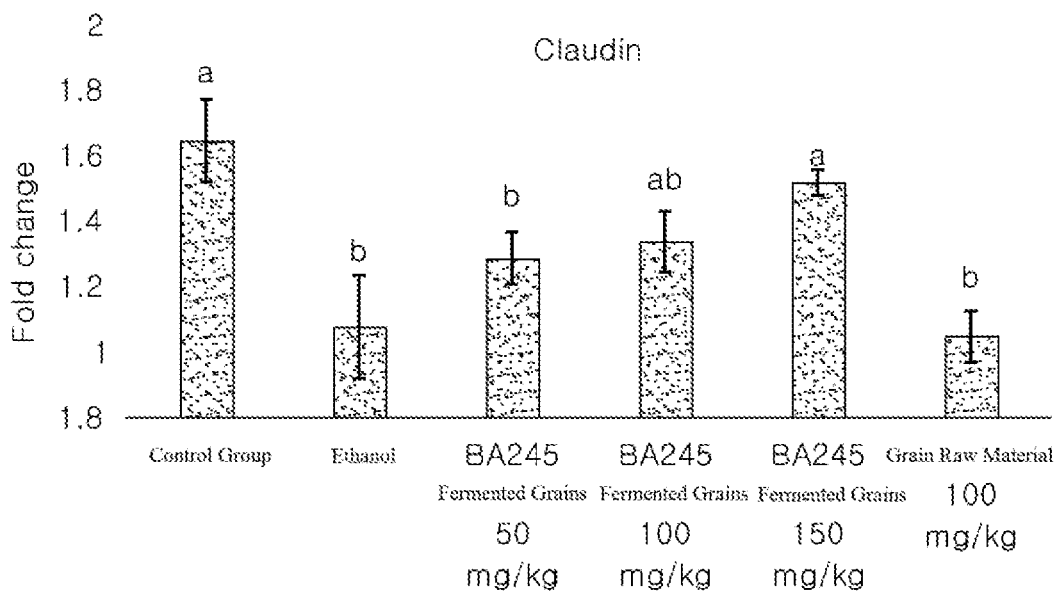
(b)
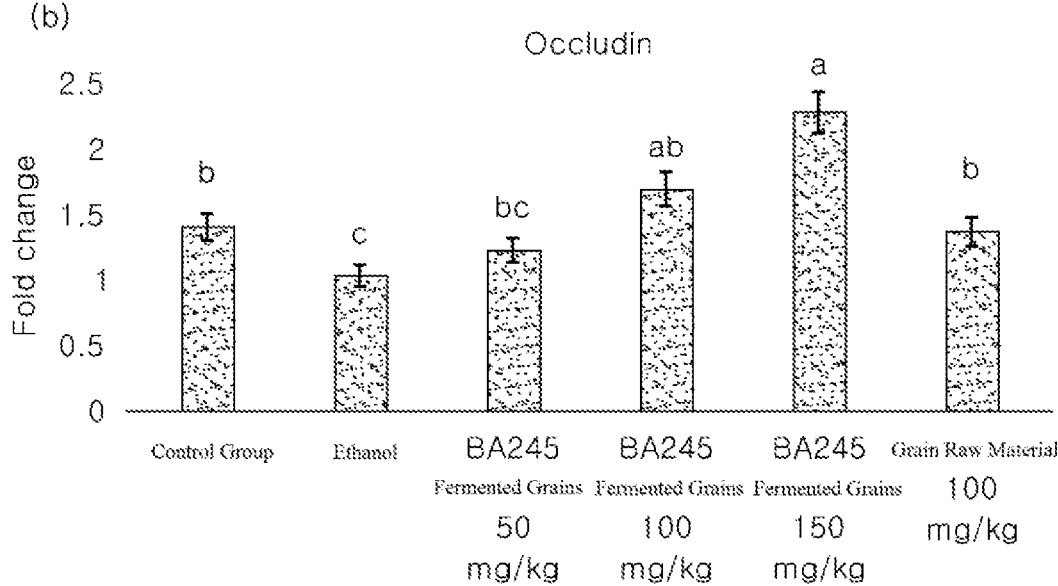

[Fig. 9]
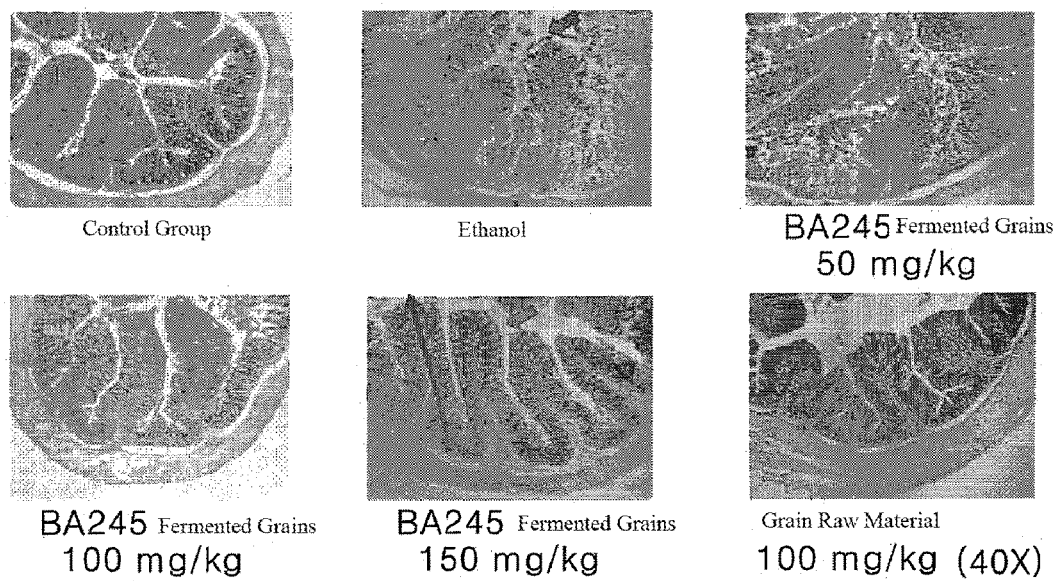
[Fig. 10]
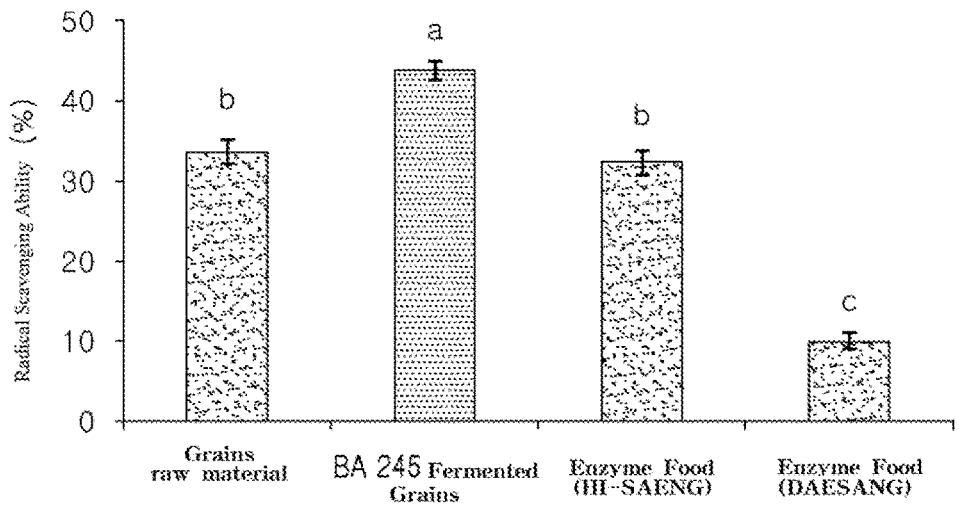

SEQUENCE LISTING

```
<160> NUMBER OF SEQ ID NOS: 3

<210> SEQ ID NO 1
<211> LENGTH: 1420
<212> TYPE: RNA
<213> ORGANISM: Artificial Sequence
<220> FEATURE:
<223> OTHER INFORMATION: 16S rRNA gene of Bacillus amyloliquefaciens
      BA245

<400> SEQUENCE: 1
agtcgagcgg  acagatggga  gcttgctccc  tgatgttagc  ggcggacggg  tgagtaacac      60
gtgggtaacc  tgcctgtaag  actgggataa  ctccgggaaa  ccggggctaa  taccggatgg     120
ttgtttgaac  cgcatggttc  agacataaaa  ggtggcttcg  gctaccactt  acagatggac     180
ccgcggcgca  ttagctagtt  ggtgaggtaa  cggctcacca  aggcgacgat  gcgtagccga     240
cctgagaggg  tgatcggcca  cactgggact  gagacacggc  ccagactcct  acgggaggca     300
gcagtaggga  atcttccgca  atggacgaaa  gtctgacgga  gcaacgccgc  gtgagtgatg     360
aaggttttcg  gatcgtaaag  ctctgttgtt  agggaagaac  aagtgccgtt  caaatagggc     420
ggcaccttga  cggtacctaa  ccagaaagcc  acggctaact  acgtgccagc  agccgcggta     480
atacgtaggt  ggcaagcgtt  gtccggaatt  attgggcgta  aagggctcgc  aggcggtttc     540
ttaagtctga  tgtgaaagcc  cccggctcaa  ccggggaggg  tcattggaaa  ctggggaact     600
tgagtgcaga  agaggagagt  ggaattccac  gtgtagcggt  gaaatgcgta  gagatgtgga     660
ggaacaccag  tggcgaaggc  gactctctgg  tctgtaactg  acgctgagga  gcgaaagcgt     720
ggggagcgaa  caggattaga  taccctggta  gtccacgccg  taaacgatga  gtgctaagtg     780 ttaggggggtt  tccgccccctt  agtgctgcag  ctaacgcatt  aagcactccg  cctggggagt     840
acggtcgcaa  gactgaaact  caaaggaatt  gacggggggcc  cgcacaagcg  gtggagcatg     900
tggtttaatt  cgaagcaacg  cgaagaacct  taccaggtct  tgacatcctc  tgacaatcct     960
agagatagga  cgtccccttc  gggggcagag  tgacaggtgg  tgcatggttg  tcgtcagctc    1020
gtgtcgtgag  atgttgggtt  aagtcccgca  acgagcgcaa  cccttgatct  tagttgccag    1080
cattcagttg  ggcactctaa  ggtgactgcc  ggtgacaaac  cggaggaagg  tggggatgac    1140
gtcaaatcat  catgccccctt  atgacctggg  ctacacacgt  gctacaatgg  acagaacaaa    1200
gggcagcgaa  accgcgaggt  taagccaatc  ccacaaatct  gttctcagtt  cggatcgcag    1260
tctgcaactc  gactgcgtga  agctggaatc  gctagtaatc  gcggatcagc  atgccgcggt    1320
gaatacgttc  ccgggccttg  tacacaccgc  ccgtcacacc  acgagagttt  gtaacacccg    1380
aagtcggtga  ggtaaccttt  aggagccagc  cgccgaaggt                            1420

<210> SEQ ID NO 2
<211> LENGTH: 24
<212> TYPE: DNA
```

```
<213> ORGANISM: Artificial Sequence
<220> FEATURE:
<223> OTHER INFORMATION: Forward primer

<400> SEQUENCE: 2
cagtcaggaa atgcgtacgt cctt                                          24

<210> SEQ ID NO 3
<211> LENGTH: 24
<212> TYPE: DNA
<213> ORGANISM: Artificial Sequence
<220> FEATURE:
<223> OTHER INFORMATION: Reverse primer

<400> SEQUENCE: 3
caaggtaatg ctccaggcat tgct                                          24
```

STRAIN DERIVED FROM TRADITIONAL FERMENTED FOOD AND HAVING EXCELLENT ENZYME PRODUCTIVITY, AND METHOD FOR PREPARING FERMENTED CEREAL ENZYME FOOD BY USING SAME

CROSS-REFERENCE TO RELATED APPLICATIONS

The present specification is a U.S. National Stage of International Patent Application No. PCT/KR2016/012109 filed Oct. 26, 2016, which claims priority to and the benefit of Korean Patent Application No. 10-2015-0148663 filed in the Korean Intellectual Property Office on Oct. 26, 2015, the entire contents of which are incorporated herein by reference.

The Sequence Listing created on Apr. 23, 2018 with a file size of 3 KB, and filed herewith in ASCII text file format as the file entitled "40E2575.txt" is hereby incorporated by reference in its entirety.

TECHNICAL FIELD

The present disclosure relates to a novel strain of *Bacillus amyloliquefaciens*, a method of producing fermented grains using the strain, fermented grains comprising the strain, and a composition for thrombolysis; digestion improvement; prophylaxis, amelioration or treatment of bowel inflammation, weakened serous membrane or intestinal injury; or antioxidation, which comprises the stain or the fermented grains.

BACKGROUND ART

Enzymes are important proteins that are associated with in vivo metabolic activity and catalyze chemical reactions. Enzymes are broadly categorized into food enzymes which are not made in the body and should be ingested from outside, digestive enzymes which are made in the body and serve to digest food, and metabolic enzymes which carry out functions required for metabolic activity except digestion. Thereamong, food enzymes have been reported to perform physiological activities such as digestion/absorption activity, decomposition/discharge activity, anti-inflammatory and antibacterial activity, detoxification/sterilization activity, blood purification activity, cell activation, and the like (Shin Hyun Jae, Enzyme Treatment, p. 29-41, 2013).

Enzyme food refers to food which contains a plenty of enzymes by culturing edible microorganisms in edible raw materials in order to enhance functions of enzymes, enzyme-containing substances which are extracted from foods, or processed substances thereof. Such enzyme food is reported to have increased amounts of various micronutrient elements and physiologically active substances which aid in both production of various physiologically active substances and nutrients through fermentation and ageing by enzymes in food and microorganisms and digestion and absorption through proliferation of beneficial bacteria (Huh, S. H. and Kim, M. H. The modern health and health food, 1997. Hongikjea Press. Korea, p. 35-36).

Under such circumstances, the present inventors conducted extensive research to develop fermented grains capable of being utilized as enzyme food, and as a result, the present inventors have successfully screened strains with excellent starch and protein degradation capability, and produced fermented grains using the same, from which various effects are identified, which leads to the present disclosure.

DISCLOSURE

Technical Problem

It is an aspect of the present disclosure to provide a novel strain of *Bacillus amyloliquefaciens* BA245.

It is another aspect of the present disclosure to provide a method of producing fermented grains, comprising: (a) inoculating a grain with the strain according to the present disclosure; and (b) culturing the strain to obtain fermented grains.

It is a further aspect of the present disclosure to provide fermented grains comprising the strain according to the present disclosure.

It is yet another aspect of the present disclosure to provide a composition for thrombolysis; digestion improvement; prophylaxis, amelioration or treatment of bowel inflammation, serous membrane weakening or intestinal injury; or antioxidation, comprising the strain or fermented grains according to the present disclosure, and a food composition (for example, enzyme food composition) comprising the strain or fermented grains according to the present disclosure.

Technical Solution

In accordance with one aspect of the present disclosure, there is provided a strain of *Bacillus amyloliquefaciens* BA245 (KCTC 12905BP).

Specifically, the strain *Bacillus amyloliquefaciens* BA245 produces starch and protein degrading enzymes with strong activity and hydrolyzes high molecular weight carbohydrates and proteins into low molecular weight substances such as saccharides which are feasible to be used by microorganisms so as to aid microorganisms' function and low molecular weight peptides, thereby significantly increasing digestion and absorption rate. Further, since *Bacillus amyloliquefaciens* BA245 can modify proteins which constitute bacteria while actively grow using carbohydrates which are main constituents of a grain, the content of crude proteins in enzyme food can be relatively increased. The content of dietary fibers is also increased by fermentation using BA245, wherein dietary fibers have laxative properties and are important nutrients for beneficial bacteria in intestines, and increase the number of beneficial bacteria, thereby helping beneficial bacteria create a healthy intestinal environment.

*Bacillus amyloliquefaciens* BA245 according to the present disclosure is the strain with the best starch and protein degradation enzyme production ability selected from strains derived from Korean traditional fermented food, and is isolated from yeast.

In order to identify selected BA245, genetic sequencing of 16S rRNA was performed, and as a result, BA245 was found to have a 16S rRNA gene sequence set forth in SEQ ID NO: 1, and subsequently, based on the sequence, sequence homology comparison with known strains and phylogenic relationship analysis were carried out, and as a result, BA245 was found to have 99.9% identity with *Bacillus amyloliquefaciens* (see FIG. 2) and the highest relationship with *Bacillus amyloliquefaciens* through comparison with the gyrase A gene sequence (see FIG. 3).

BA245 according to the present disclosure was designated as *Bacillus amyloliquefaciens* BA245 and was deposited at the Korean Culture for Type Cultures (KCTC) on Sep. 23, 2015 under accession number KCTC12905BP under the provisions of the Budapest Treaty.

In accordance with another aspect of the present disclosure, there is provided a method of producing fermented grains, comprising: (a) inoculating a grain with *Bacillus amyloliquefaciens* BA245 deposited under accession number KCTC 12905BP; and (b) culturing the strain to obtain fermented grains.

The production method according to the present disclosure will be described in stepwise detail as follows.

Step (a): Inoculating Grain with Strain

The grain which can be used in step (a) may include at least one selected from the group consisting of wheat, wheat germ, wheat bran, white rice, brown rice, germinated brown rice, barley, oats, red rice, sticky black rice, sticky rice, rice bran, soybean, black soybean, black beans, quinoa, lentils, and adlay. The grain may be used in crushed form, in powder form, or used per se without crushing.

Specifically, in step (a), the grain may include wheat germ and wheat bran. In this case, wheat germ and wheat bran may be present in an amount of 40 parts by weight to 100 parts by weight, 50 parts by weight to 100 parts by weight, 50 parts by weight to 90 parts by weight, 50 parts by weight to 80 parts by weight or 60 parts by weight to 80 parts by weight relative to 100 parts by weight of the grain.

More specifically, in step (a), the grain may further include at least one grain selected from the group consisting of oats, lentils, brown rice, sticky barley, and quinoa, in addition to wheat germ and wheat bran. The additional the grain may be present in an amount of 1 part by weight to 20 parts by weight, specifically, 3 parts by weight to 10 parts by weight relative to 100 parts by weight of the grain. In addition, in step (a), the grain may have a moisture content of 30% (v/w) to 70% (v/w). Specifically, the grain may have a moisture content of 30% (v/w) to 60% (v/w), 30% (v/w) to 50% (v/w), or 30% (v/w) to 40% (v/w). If the moisture content is less than 30%, fermentation rate of *bacillus* can be delayed due to low moisture, particularly, due to moisture evaporated during fermentation, the level of moisture can reach 20%, making it difficult to grow *bacillus* after completion of fermentation. If the moisture content is higher than 70%, drying can be costly.

Specifically, moisture can stem from the grain, pretreatment to introduce moisture to the grain, or further treatment to add moisture to the grain in step (a) (namely, the grain in step (a) may be gain subjected to moisture treatment). Moisture treatment may be performed by directly spraying an appropriate amount of water onto the grain or mixing the grain with water.

In addition, the method of producing fermented grains according to the present disclosure may further comprise heat treating the grain prior to step (a). Although strain culturing is feasible in the grain without heat treatment, the heat treatment enables not only sterilization of infectious microbes in the grain, but also can break down grain cell walls, perform gelatinization and protein denaturation and provide environments capable of actively growing microorganisms, thereby decreasing strain inoculation amount, which in turn leads to cost reduction. The heat treatment may be performed by various known methods in the art, for example, using steam or superheated steam. Specifically, the heat treatment is performed using steam at 70° C. to 140° C. for 10 minutes to 60 minutes or superheated steam at 200° C. to 300° C. for several seconds to several minutes. More specifically, the heat treatment is performed using steam at 70° C. to 130° C. for 20 minutes to 60 minutes, or steam at 80° C. to 125° C. for 20 minutes to 45 minutes. If the heat treatment temperature is lower or the treatment time is shorter than the above range, sterilization effects for infectious microbes can be deteriorated, thereby preventing the subsequent fermentation process from smoothly proceeding; whereas if the heat treatment temperature is higher or the heat treatment time is longer that the above range, efficiency of fermentation is lowered due to protein denaturation in grain, thereby deteriorating quality of final products.

In addition, the method of producing fermented grains according to the present disclosure may further comprise heat treatment after treating the grain with moisture prior to step (a). The moisture treatment and heat treatment are as described above.

Then, the grain is inoculated with a strain of *Bacillus amyloliquefaciens* BA245 deposited under accession number KCTC 12905BP.

Prior to the inoculation, the method may further comprise cooling optionally heat treated grain. Cooling may be performed naturally after heat treatment, or by increasing a cooling speed to prevent superheating so as to ensure homogenous cooling (for example, using a conveyor cooler). Specifically, cooling is performed at a temperature of 30° C. to 50° C., 35° C. to 45° C., or 35° C. to 40° C.

Inoculation of grains with *Bacillus amyloliquefaciens* BA245 may be performed using a pre-cultured strain solution, an isolated strain, a powder shaped strain in a lyophilized state, or a cultured mass thereof. The inoculation amount of BA245 is determined such that the number of bacteria directly after inoculation is $1 \times 10^5$ CFU/g to $1 \times 10^{10}$ CFU/g, or $1 \times 10^6$ CFU/g to $1 \times 10^9$ CFU/g. If the inoculation amount is less than $1 \times 10^5$ CFU/g, a less amount of the seed bacteria-fermented solution is required, whereas much time is required to ferment the grains, thereby requiring a long fermentation time in production of products, which in turn increases a possibility of infectious microbe contamination. On the contrary, if the inoculation amount is greater than $1 \times 10^{10}$ CFU/g, the fermentation time can be considerably shortened, whereas seed bacteria for implantation impose a burden on production costs.

Step (b): Culturing Strain to Obtain Fermented Grains

After step (a), the strain according to the present disclosure may be cultured with the grain to obtain fermented grains. As can be seen from Examples below, *Bacillus amyloliquefaciens* BA245 according to the present disclosure is cultured in the grain to provide fermented grains due to excellent starch degradation enzyme activity and protein degradation enzyme activity possessed by the strain, thereby enhancing digestion and absorption rate through conversion of proteins in the fermented grains into small molecules; and the fermented grains includes various efficient components such as dietary fibers and possesses advantageous activities, such as thrombolysis; digestion improvement; prophylaxis, amelioration or treatment of bowel inflammation, serous membrane weakening or intestinal injury; or antioxidation.

Culturing may be liquid culturing or solid culturing, specifically, solid culturing. Culturing may be performed at a temperature of 20° C. to 50° C., 30° C. to 45° C. or 37° C. for 1 hour to 48 hours, 6 hours to 48 hours, 6 hours to 36 hours, 12 hours to 36 hours, 12 hours to 30 hours, 18 hours to 30 hours, 22 hours to 26 hours, or 24 hours.

Culturing may be performed using, for example, a liquid phase culture tank, a rotary drum fermenter, or a tray fermenter, without being limited thereto. In addition to the rotary drum or the tray fermenter, any type of fermenter may be used without limitation so long as the fermenter is useful for fermentation of the grain or mixtures thereof, and is suitably selected depending upon production scale.

The method according to the present disclosure may further include drying and/or crushing the fermented grains obtained in step (b). Drying and/or crushing may be performed by various methods known in the art. However, if drying is performed at an excessively high temperature, attention must be paid since viable microbes in the fermented grains can be sterilized to decrease enzyme activity. Specifically, drying may be performed at low temperature such that the strain according to the present disclosure is not sterilized while maintaining enzyme activity, and drying may be performed at a low temperature of, for example, 40° C. to 75° C., or 50° C. to 70° C. with low humidity hot air such that the fermented grains have a moisture content of 20% or less, or 10% or less. Crushing may be performed so as to crush the fermented grains in various sizes, as needed, using, for example, a hammer mill.

In accordance with a further aspect of the present disclosure, there is provided fermented grains comprising *Bacillus amyloliquefaciens* BA245 deposited under accession number KCTC 12905BP.

Specifically, *amyloliquefaciens* BA245 may be a cultured mass or a crushed mass thereof, and the like. The following description will be given of BA245.

The fermented grains according to the present disclosure may further include: (a) 50 wt % to 60 wt % of carbohydrates; (b) 20 wt % to 30 wt % of crude proteins; (c) 50 to 200 mg/100 g of lysine; (d) 15 to 150 mg/100 g of isoleucine; (e) 100 to 300 mg/100 g of leucine; (f) 10 to 70 mg/100 g of methionine; (g) 100 to 300 mg/100 g of phenylalanine; (h) 50 to 100 mg/100 g of tryptophan; and (i) 50 to 300 mg/100 g of valine. Specifically, the fermented grains according to the present disclosure may further include: (j) 25 wt % to 30 wt % of dietary fibers; and (k) 3 to 80 mg/100 g of threonine. More specifically, in the fermented grains, carbohydrates may be present in an amount of 53 wt % to 60 wt %, dietary fibers may be present in an amount of 26 wt % to 29 wt %, and crude proteins may be present in an amount of 21 to 25 wt %. As essential amino acids, threonine may be present in an amount of 40 to 70 mg/100 g, or 40 to 60 mg/100 g; lysine may be present in an amount of 70 to 150 mg/100 g, or 100 to 150 mg/100 g; isoleucine may be present in an amount of 70 to 120 mg/100 g, or 80 to 110 mg/100 g; leucine may be present in an amount of 150 to 250 mg/100 g, or 170 to 240 mg/100 g; methionine may be present in an amount of 30 to 60 mg/100 g, or 40 to 50 mg/100 g; phenylalanine may be present in an amount of 150 to 250 mg/100 g, or 170 to 240 mg/100 g; tryptophan may be present in an amount of 60 to 90 mg/100 g, or 65 to 85 mg/100 g; and valine may be present in an amount of 150 to 250 mg/100 g, or 170 to 240 mg/100 g.

In the fermented grains, peptides having MW of 5 kDa or less may be present in an amount of 50 to 80 parts by weight relative to 100 parts by weight of crude proteins, and peptides having MW of 30 kDa or more may be present in an amount of 5 to 20 parts by weight relative to 100 parts by weight of crude proteins. Specifically, peptides having MW of 5 kDa or less may be present in an amount of 55 to 70 parts by weight relative to 100 parts by weight of crude proteins, and peptides having MW of 30 kDa or more may be present in an amount of 5 to 15 parts by weight relative to 100 parts by weight of crude proteins.

Further, the fermented grains may possess alpha-amylase activity of 2,000 U/g to 4,000 U/g, 2,300 U/g to 3,500 U/g, 2,500 U/g to 3,500 U/g, or 2,500 U/g to 3,000 U/g.

Furthermore, the fermented grains may possess protease activity of 2,000 U/g to 4,000 U/g, 2500 U/g to 4,000 U/g, 3,000 U/g to 4,000 U/g, 3500 U/g to 4,000 U/g, or 3700 U/g to 4,000 U/g.

The fermented grains according to the present disclosure may be produced by the method of producing fermented grains according to the present disclosure as set forth above.

In accordance with yet another aspect of the present disclosure, there is provided a food composition comprising the strain or fermented grains according to the present disclosure. The food composition is not particularly limited so long as the composition is edible.

Specifically, the food composition may be enzyme food. The term "enzyme food" refers to food which contains a plenty of enzymes by culturing edible microorganisms in an edible raw material in order to reinforce functions of enzymes, enzyme-containing portions which are extracted from food, or processed substances thereof.

The food composition according to the present disclosure may include a health food composition. When the strain or fermented grains according to the present disclosure is used in food or in a health food composition, the strain or fermented grains according to the present disclosure may be added per se, or together with other food or food components, and may be suitably used according to typical methods. The amount of the strain or fermented grains according to the present disclosure to be mixed may be suitably determined depending upon intended use (prophylaxis, health or treatment). Any food composition may be included without any limitation so long as the food composition is edible. Examples of the food composition may include meats, sausages, breads, cakes, chocolates, candies, snacks, confectionaries (cookies, crackers, and the like), pizza, noodles (ramen and the like), gum, dairy products including ice-cream, various soups, ketchups, sauces, gravies, dressings, beverages, teas, tonic drinks, alcoholic beverages, vitamin complexes, and the like.

The food or health food composition according to the present disclosure may further include various flavoring agents or natural carbohydrates, like typical beverages. Natural carbohydrates refer to monosaccharides such as glucose and fructose, disaccharides such as maltose and sucrose, polysaccharides such as dextrin and cyclodextrin, and sugar alcohols such as xylitol, sorbitol and erythritol and the like. Examples of sweetening agents may include natural sweetening agents such as thaumatin or stevia extract, synthetic sweetening agents such as saccharin or aspartame, and the like. The natural carbohydrates are generally present in an amount of about 0.01 to 0.20 g, specifically, about 0.04 to 0.10 g, based on 100 ml of the food or health food composition according to the present disclosure.

The food or health food composition according to the present disclosure may also include various nutritional supplements, vitamin, electrolytes, flavors, coloring agents, pectic acid and salts thereof, alginic acid and salts thereof, organic acids, protective colloidal thickeners, pH modifying agents, stabilizers, preservatives, glycerin, alcohol, carbonating agents used in carbonated drinks, and the like. In addition, the food or health food composition according to the present disclosure may include fruit flesh for the preparation of natural fruit juice, fruit juice beverages, and vegetable beverages. Those components may be used alone or in combination thereof. Such additives may be present in an amount of 0.01 to 0.20 parts by weight relative to 100 parts by weight of the food or health food composition.

In accordance with yet another aspect of the present disclosure, there is provided a composition for thrombolysis;

digestion improvement; prophylaxis, amelioration or treatment of bowel inflammation, weakened serous membrane or intestinal injury; or antioxidation, comprising the stain *Bacillus amyloliquefaciens* BA245 or the fermented grains comprising the stain *Bacillus amyloliquefaciens* BA245.

As used herein, the term "prophylaxis" means all behavior for inhibiting or delaying occurrence of disease, and the term "amelioration" means all behavior for reducing or relieving symptoms of disease and side effects thereof. The term "treatment" means all behavior for improving or beneficially changing symptoms of disease and side effects thereof.

As could be seen from Examples below, the strain or fermented grains according to the present disclosure specifically had fibrinolytic activity (Example 8); improved gastric emptying ability of solid substances (Example 9); improved intestinal permeability in acute enteritis animal models (Example 10), enhanced serous membrane (Example 11); treated injury in intestinal tissues (Example 12); and had high antioxidant activity (Example 13). Accordingly, it can be seen that the strain or fermented grains according to the present disclosure possesses thrombolysis; digestion improvement; prophylaxis, amelioration or treatment of bowel inflammation, serous membrane weakening or intestinal injury; and antioxidant activity, and thus can be used as medicine and food (or functional health foods) for thrombolysis; digestion improvement; prophylaxis, amelioration or treatment of bowel inflammation, serous membrane weakening or intestinal injury; or antioxidation.

Specifically, the composition for thrombolysis may be effective for prophylaxis or treatment of myocardial infarction, venous thrombosis, stroke, cerebral infarction, cerebral thrombosis, or cerebral embolism due to thrombolysis function thereof.

The composition according to the present disclosure may be administered by oral or parenteral routes (for example, intravenously, subcutaneously, intra-peritoneally or topically) according to intended methods, and specifically, the composition is orally administered.

When the composition according to the present disclosure is a pharmaceutical composition, the composition may further comprise at least one pharmaceutically acceptable carrier in addition to the strain or fermented grains according to the present disclosure. The pharmaceutically acceptable carrier may be saline solutions, sterilized water, Ringer's solutions, buffered saline solutions, dextrose solutions, maltodextrin solutions, glycerol, ethanol and a mixture of at least one thereof, and if desired, may include other typical additives such as antioxidants, buffer solutions, bacteriostatic agents, and the like. In addition, the composition according to the present disclosure may be formulated into formulations for injection such as aqueous solutions, suspensions, emulsions, and the like, pills, capsules, granules or tablets by additionally introducing diluents, dispersing agents, surfactants, binding agents and lubricants. Furthermore, the composition according to the present invention may be formulated depending upon each disease or each component by employing an appropriate method known in the art or a method described in *Remington's Pharmaceutical Science* (22nd), Mack Publishing Company, Easton Pa.

The pharmaceutical composition according to the present disclosure may be used alone or in combination with surgeries, hormone treatments, medicine treatments and methods employing biological reaction modifying agents.

In accordance with yet another aspect of the present disclosure, there is provided a method for treatment, amelioration or prophylaxis of disease due to blood clot; digestive function improvement; prophylaxis, amelioration or treatment of bowel inflammation, serous membrane weakening or intestinal injury; or active oxygen reduction, comprising administering a composition comprising a strain of *Bacillus amyloliquefaciens* BA245 or fermented grains produced using the strain and a pharmaceutically or cytologically acceptable carrier to a subject in need thereof. According to the present disclosure, administration may be performed by administering the composition according to the present disclosure in various dosages depending upon body weight, age, gender, physical condition, and diet of patients, administration hours, administration method, emptying rate and severity of diseases, and the like. The fermented grains according to the present disclosure may be administered once to several times per day at a dosage of about 0.0001 to 600 mg/kg, or about 0.001 to 500 mg/kg. Further, the strain according to the present disclosure may be administered in an amount of $5 \times 10^4$ CFU/ml to $5 \times 10^8$ CFU/ml, or $1 \times 10^6$ CFU/ml to $1 \times 10^8$ CFU/ml, may be administered in an amount of 30 ml to 100 ml per administration or in an amount of 50 ml to 100 ml per administration, and may be administered once to four times daily.

Advantageous Effects (a) The present disclosure provides a novel strain of *Bacillus amyloliquefaciens* BA245 (KCTC12905BP) having excellent starch degradation enzyme activity and protein degradation enzyme activity, a method of producing fermented grains using the strain, fermented grains comprising the strain, and various functional compositions comprising the strain or the fermented grains.

(b) If fermented grains is produced using the strain as a seed bacteria, the resulting fermented grains has increased amounts of low molecular weight substances and crude proteins derived from hydrolysis of carbohydrates and protein, and thus is effective for treatment or prophylaxis of disease due to blood clot, digestion improvement, prophylaxis, amelioration or treatment of bowel inflammation, serous membrane weakening or intestinal injury, or antioxidation.

(c) Thus, the present disclosure can provide high quality medicine and food (or health food), which can provide assistance to nutrient ingestion, thrombolysis, digestion improvement, intestinal health and antioxidant activity, using the fermented grains.

DESCRIPTION OF DRAWINGS

FIG. 1 shows selection results on alpha-amylase plate media (FIG. 1A) and protease plate media (FIG. 1B) in order to select strains which highly produce starch degradation enzymes and protein degradation enzymes at the same time.

FIG. 2 shows a phylogenic tree illustrating a phylogenic relationship based on 16S rRNA gene sequence.

FIG. 3 shows a phylogenic tree illustrating a phylogenic relationship based on gyrase A gene sequence suitable for phylogeny of strains in genus *bacillus*.

FIG. 4 shows chromatography results for the content of low molecular weight peptides of BA245 fermented grains compared with that of raw materials and BA474 fermented grains in which BA474 is a homologous strain.

FIG. 5 shows fibrin plate analysis results illustrating thrombolysis activity.

FIG. 6 shows a bar graph illustrating fibrinolytic activity.

FIG. 7 shows intestinal permeability evaluation results depending upon the content of BA245 fermented grains.

FIG. 8 shows degree of expression of claudin (FIG. 8a) and occludin (FIG. 8b) which are tight junction proteins of intestinal cells, in which the degree of expression represents the degree of serous membrane reinforcement.

FIG. 9 includes photographs illustrating histological observation of recovery of intestine epidermal injury by ingesting BA245 fermented grains.

FIG. 10 shows test results for antioxidant activity (radical scavenging ability) of the grain raw materials, BA245 fermented grains and enzyme food, respectively.

MODE FOR INVENTION

Hereinafter, the present disclosure will be described in more detail with reference to the following examples. It should be understood that these examples are provided for illustration only and are not to be construed in any way as limiting the present disclosure.

Example 1: Selection of Strain Capable of Highly Producing Starch and Protein Degradation Enzymes In order to isolate strains having high starch and protein degradation enzyme production ability, the present inventors isolated about 3,000 species of microorganisms from various kinds of Korean traditional fermented food (kimchi, jang, yeast, Korean traditional liquor, salted sea foods, and the like), and tried to screen strains possessing high expression degree of starch and protein degradation enzymes mainly from about 1308 species of *bacillus* suitable for food.

Selection of strains having high starch and protein degradation enzyme production ability was performed by comparing size of transparent circles formed by decomposition of substrates (raw materials) in a YM agar medium (3.0 g of yeast extract, 3.0 g of malt extract, 5.0 g of peptone, 10.0 g of dextrose, 20.0 g of agar) containing 1% (w/v) of soluble starch (Difco, USA) or 2% (w/v) of skim milk (Difco, USA).

Specifically, TSB media (17.0 g of enzymatic digest of casein, 3.0 g of enzymatic digest of soybean meal, 5.0 g of NaCl, 2.5 g of dipotassium phosphate, 2.5 g of dextrose, final pH: 7.3±0.2 at 25° C.) were inoculated with each strain, cultured at 37° C. at 200 rpm for 12 hours, followed by spotting the culture solution by 1.0 µl to the YM agar medium containing a soluble starch and skim milk. After culturing the agar medium at 37° C. for 16 hours, the diameter of transparent circles formed on the medium was measured.

As a result, strain BA245 which exhibited 5.85 mm diameter transparent circles on 1% (w/v) soluble starch medium and 6.14 mm diameter transparent circles on 2% (w/v) skim milk (Difco, USA) medium and possessed excellent starch and protein degradation enzyme activity was selected as a strain for the grain fermentation (FIGS. 1a and 1b).

Example 2: Identification of Strain BA245

2-1. 16S rRNA Gene Sequencing of Strain BA245

In order to identify the strain BA245 selected in Example 1, 16S RNA gene sequencing was requested to Korean Culture of Microorganisms (KCCM) affiliated with Korean Federation of Culture Collections (KFCC), thereby obtaining a 1420 bp nucleotide sequence (SEQ ID NO: 1) including a 50 to 900 bp nucleotide sequence required for the identification. In addition, the sequence was registered in the database of NCBI GenBank under accession number KR535604.

2-2. Analysis of Phylogenic Tree According to 16S rRNA Gene Sequencing of Strain BA245

In order to analyze phylogenic taxon of strain BA245, 16S rRNA gene sequences of reference strains of various species which are close to strain BA245 in genus *Bacillus* were investigated using sequence data registered with GenBank, and these gene sequences were aligned using Bioedit (Hall, 1999) and Clustal X (Thompson et al., 1997). Evolution procedures of strains were pursued using the Kimura two-parameter model (Kimura, 1983), and phylogenic taxon of strains was determined using neighbor-joining and maximum parsimony method of Phylogenic tree (FIG. 2).

2-3. Phylogenic Tree Analysis of Gyrase a (Gyr A) Gene Sequence of Strain BA245

Identification of Strain BA245 was Performed Using Phylogenic Analysis Based on Gyrase a Gene Sequence.

In order to analyze gyrase A gene sequence, a forward primer (SEQ ID NO: 2: 5'-CAG TCA GGA AAT GCG TAC GTC CTT-3') and a reverse primer (SEQ ID NO: 3: 5'-CAA GGT AAT GCT CCA GGC ATT GCT-3') were constructed, and then Microgen Inc. performed sequence analysis of gyrase A. Gyrase A gene sequences of reference strains of various species close to strain BA245 in genus *Bacillus* were investigated using sequence data registered with GenBank, and these gene sequences were aligned using Bioedit (Hall, 1999) and Clustal X (Thompson et al., 1997). Development procedures of strains were chased using the Kimura two-parameter model (Kimura, 1983) and phylogenic taxon of strains was determined using neighbor-joining and maximum parsimony method of phylogenic tree (Kimura et al., 2004) (FIG. 3).

2-4. Analysis of Biochemical Properties of BA245 Using API Kit

Biochemical properties of *Bacillus amyloliquefaciens* BA245 were examined using API 50CH (bioMerieux Co., France) used in identification of *Bacillus*. API kit was used in accordance with manufacturer's guidelines, and results thereof are summarized in Table 1 below.

A TSB liquid medium (17.0 g if enzymatic digest of casein, 3.0 g of enzymatic digest of soybean meal, 5.0 g of NaCl, 2.5 g of dipotassium phosphate, 2.5 g of dextrose, final pH: 7.3±0.2 at 25° C.) was inoculated with *Bacillus amyloliquefaciens* BA245, cultured at 37° C., dispensed to Eppendorf tubes, and then centrifuged at 10,000 rpm for 5 minutes to collect cells, which were washed once with a sterilized saline solution (0.85%). The cells were suspended in sterilized distilled water, and an ampoule of API 50CH medium aseptically broken was inoculated with the suspension, followed by pipetting homogenously, which in turn was dispensed in an amount of 150 µl to microtubes of each test strip. After cells were dispensed, the cells were cultured in an incubator at 37° C. for 24 to 48 hours and color change was investigated using API kit.

TABLE 1

| Property | Result | Property | Result |
| --- | --- | --- | --- |
| Glycerol | + | Salicin | + |
| Erythritol | − | Cellobiose | + |
| D-arabinose | − | Maltose | + |
| L-arabinose | + | Lactose | + |
| Ribose | + | Melibiose | (+) |
| D-xylose | + | Sucrose | + |
| L-xylose | − | Trehalose | + |
| Adonitol | − | Inulin | − |
| Methyl-B-D-xylopyranside | − | Melezitose | − |

TABLE 1-continued

| Property | Result | Property | Result |
|---|---|---|---|
| Galactose | (+) | Raffinose | + |
| Glucose | + | Starch | + |
| Fructose | + | Glycogen | + |
| Mannose | + | Xylitol | − |
| Sorbose | − | Gentiobiose | + |
| Rhamnose | − | D-turanose | (+) |
| Dulcitol | − | D-lyxose | − |
| Inositol | + | D-tagatose | − |
| Mannitol | + | D-fucose | − |
| Sorbitol | + | L-fucose | − |
| Methyl-α,D-Mannopyranside | − | D-arabitol | − |
| Methyl-α,D-glucoside | + | L-arabitol | − |
| N-acetyl-glucosamine | + | Gluconate | − |
| Amygdalin | + | 2-keto-gluconate | − |
| Arbutin | + | 5-keto-gluconate | (+) |
| Esculin | + | | |

2-5. Results of Identification

Considering the overall results of biochemical properties and phylogenic relationship analysis, the selected strain was designated as *Bacillus amyloliquefaciens* BA245 and was deposited at the Korean Collection for Type Cultures (KCTC) on Sep. 23, 2015 under accession number KCTC12905BP under the provisions of the Budapest Treaty.

Example 3: Production of Fermented Grains Using Strain BA245

Fermented grains was produced using *Bacillus amyloliquefaciens* BA245 (hereinafter referred to as 'strain BA245') selected in Example 2 as follows.

First, moisture was added to 300 g of grains [wheat bran; wheat germ; oats; brown rice; quinoa; lentils; sticky barley; wheat germ and wheat bran grain mixture (60 wt % of wheat germ and 40 wt % of wheat bran); and an entire grain mixture (40 wt % of wheat germ, 30 wt % of wheat bran, 10 wt % of oats, 5 wt % of lentils, 5 wt % of brown rice, 5 wt % of sticky barley and 5 wt % of quinoa, hereinafter the entire the grain mixture is referred to as 'the grain raw material')], followed by steaming the grains at 121° C. for 30 minutes and then cooling to 40° C. or less. Next, the strain BA245 was streaked on a TSB agar medium (17.0 g of enzymatic digest of casein, 3.0 g of enzymatic digest of soybean meal, 5.0 g of NaCl, 2.5 g of dipotassium phosphate, 2.5 g of dextrose, 15.0 g of agar, final pH: 7.3±0.2 at 25° C.), followed by culturing at 37° C. for 12 hours, thereby activating the strain. The activated strain was suspended in 9 ml of 0.8% sterilized NaCl solution, the strain was diluted to about 0.2 in $A_{660\ nm}$ using a loop and the resulting suspension was used as seed culture. 40 ml of a TSB medium (17.0 g of enzymatic digest of casein, 3.0 g of enzymatic digest of soybean meal, 5.0 g of NaCl, 2.5 g of dipotassium phosphate, 2.5 g of dextrose, final pH: 7.3±0.2 at 25° C.) was inoculated with the seed culture suspension such that the concentration was 1%, followed by shake culturing at 37° C. and 180 rpm.

To the steamed grains in which the moisture content was adjusted to 36%, 30 ml of a culture solution (6.0×10$^7$ cfu/ml) was added and mixed sufficiently, followed by solid fermentation by stationary culturing at 37° C. for 24 hours under constant humidity conditions, thereby producing fermented grains.

Meanwhile, as a control group of strain BA245, *Bacillus amyloliquefaciens* BA474 (hereinafter referred to as 'strain' BA474) which belongs to the same species as strain BA245 was used, and fermented grains were produced using an entire the grain mixture as a raw material in the same manner as in Example 3 except that strain BA474 was used instead of strain BA245.

Example 4: Analysis of Starch Degradation Enzyme Activity

In order to analyze starch degradation enzyme activity of the fermented grains, the following experiment was performed.

Fermented grains fermented using strain BA245 and strain BA474 of Example 3 were dried in a dryer at 60° C. until the moisture content reached 10% or less, followed by crushing to obtain specimens for measurement of starch degradation enzyme activity (hereinafter referred to as 'BA245 fermented grains' and 'BA474 fermented grains' depending upon the sort of grain used in fermentation of the grain-fermented substances, wherein if an entire grain mixture (40 wt % of wheat germ, 30 wt % of wheat bran, 10 wt % of oats, 5 wt % of lentils, 5 wt % of brown rice, 5 wt % of sticky barley and 5 wt % of quinoa) was used as a raw material, the specimen was referred to as 'BA245 fermented grains' without designating raw materials, and if a grain mixture composed of grain components or a grain mixture composed of wheat germ and wheat bran was used as a raw material, the specimen was referred to as 'BA245 fermented grains' with raw materials designated in parentheses. Starch degradation enzyme activity was measured in accordance with the enzyme food alpha-amylase test method described in "Standards and specifications of foods".

Specifically, 5.0 g of each specimen was precisely weighed, dissolved in water to produce 100 ml of a solution, followed by filtering the solution, which in turn was used as a liquid specimen, while two 20 ml tubes were prepared, one for test and the other for blank test. To the test tube, 5 ml of 1% soluble starch solution, 13 ml of Mcilvaine buffer (pH 6.0) and 1 ml of 0.1% calcium chloride solution were added and warmed to 37° C., and 1 ml of liquid specimen was further added thereto, and left at 37° C. for 30 minutes, thereby preparing a reaction solution for test. Separately, in the tube for blank test, 1 ml of a liquid specimen, which was heated at 100° C. for 30 minutes to deactivate the specimen, was treated in the same manner as in the test tube, thereby preparing a reaction solution for blank test. To 0.2 ml of each reaction solution for test and blank test, 10 ml of an iodine reagent solution was added to prepare a test solution, which in turn was subjected to absorbance measurement with a liquid layer of 1 cm at a wavelength of 660 nm using water as a comparison liquid. The absorbance of the test solution should be within 0.030 of that of the blank test. If the absorbance was undetectable due to excessive color development, the absorbance was measured using a diluted liquid specimen by applying times of dilution. The content of starch was calculated using a standard curve obtained from colorimetric reaction of an iodine ($I_2$) solution, in which 1 unit of alpha-amylase was defined as an amount of enzyme to be used to digest 10 mg of starch for 30 minutes.

TABLE 2

| Sample | Alpha-amylase (U/g) |
|---|---|
| BA245 fermented grains | 2762 |
| BA245 fermented grains (grain mixture of wheat germ and wheat bran) | 2300 |
| BA474 fermented grains | 169 |

As a result, it was confirmed from Table 2 that starch degradation enzyme activity of the BA245 fermented grains and BA245 fermented grains (grain mixture of wheat germ and wheat bran) was much better than the BA474 fermented grains as a control group.

Example 5: Analysis of Protein Degradation Enzyme Activity

In order to analyze protein degradation enzyme activity of the BA254 fermented grains, the following experiment was performed.

Specimens obtained in the same manner as in Example 3 was subjected to an enzyme food protease test method prescribed in ⌈Standards and Specification of Foods⌋.

Specifically, 5.0 g of each specimen was precisely weighed, dissolved in water to produce 100 ml of a solution, followed by filtering the solution, which in turn was used as a liquid specimen. To a test tube, 1 ml of 0.6% casein solution was added and warmed in a thermostat water bath at 37° C., and 1 ml of liquid specimen was precisely weighed and added thereto, shaken sufficiently and left in a thermostat water bath at 37° C. for exactly 10 minutes. To the resulting solution, 2 ml of 0.4 M acetic trichloroacetic acid solution was added, left again at 37° C. for 25 minutes, and then filtered. 1 ml of the resulting filtered solution was precisely placed in a test tube, and 5 ml of 0.4 M sodium carbonate solution and 1 ml of Folin's reagent (prepared by diluting a stock solution three times) were added thereto, followed by shaking sufficiently. The resulting solution was left at 37° C. for 20 minutes and the resulting colored solution was used as a test solution. Separately, 1 ml of a liquid specimen was precisely weighed and placed in a test tube, and left at 37° C. for 10 minutes, and then 2 ml of 0.4 M trichloroacetic acid was added and mixed therewith. Then, 1 ml of 0.6% casein solution was added to the mixture, which in turn was left at 37° C. for 25 minutes, followed by the same treatment as in the test solution. The resulting solution was used as a solution for blank test. The absorbance was measured at a wavelength of 660 nm with a liquid layer of 1 cm using water as a comparison liquid. The absorbance of the test solution should be within 0.030 of that of the blank test. If the absorbance was undetectable due to excessive color development, the absorbance was measured using a diluted liquid specimen by applying times of dilution. A standard curve was constructed using tyrosine and protease activity was analyzed in comparison with detected tyrosine content, in which 1 unit of protease was defined as a microgram of tyrosine produced for one minute.

TABLE 3

| Sample | Protease (U/g) |
|---|---|
| BA245 fermented grains | 3868 |
| BA245 fermented grains (grain mixture of wheat germ and wheat bran) | 3481 |
| BA474 fermented grains | 106 |

As a result, it was confirmed from Table 3 that protein degradation enzyme activity of the BA245 fermented grains was much better than the BA474 fermented grains as a control group.

It was also confirmed from the results of Examples 3 and 4 that BA245 was useful for preparation of an enzyme food comprising the fermented grains having a high fermentation titer value.

Example 6: Analysis of Low Molecular Weight Protein Content

Since it was confirmed in Example 4 that fermented grains having good protein degradation enzyme activity were produced in grain fermentation using BA245, the content of proteins in the BA245 fermented grains was analyzed according to the molecular weight in order to identify whether proteins in the grain were present in hydrolyzed peptides or low molecular weight proteins.

0.1 g of the specimen of Example 3 was precisely weighed and subjected to extraction using 5 ml of 8 M urea. After centrifuging the resulting mass at 8,000 rpm for 10 minutes, the supernatant was taken and filtered with a 0.22 µm syringe filter, and finally used as a sample for analysis. The injection volume was 25 µl and a mixture of 50 mM $NaPO_4$ (pH 7.2) and 150 mM NaCl was used as a mobile phase. The flow rate was 0.5 ml/min and detection was performed at a UV wavelength of 214 nm.

As a result, it could be seen that the BA245 fermented grains had a larger peak area for low molecular weight proteins than the grain raw material and the BA474 fermented grains, thereby showing a shift of protein density to a central band side (FIG. 4). In chromatography graphs of FIG. 4, the left bands refer to high molecular weight proteins, the central bands refer to low molecular weight proteins, and the right bands refer to a solvent. Numerical data of chromatography of FIG. 4 are shown in Table 4.

TABLE 4

| | MW (kDa) | | | | |
|---|---|---|---|---|---|
| Sample | 30 or more | 10 to 30 | 5 to 10 | 5 or less | Total (%) |
| Grain raw material | 58.05 | 17.31 | 8.07 | 16.57 | 100 |
| BA245 fermented grains | 10.34 | 10.06 | 15.01 | 64.59 | 100 |
| BA474 fermented grains | 36.15 | 13.70 | 11.75 | 38.40 | 100 |

From the results, it could be seen that the high molecular weight proteins in the grain raw material were hydrolyzed by fermentation using BA245 into the low molecular weight proteins and that the degree of hydrolysis by BA245 was much better than the degree of hydrolysis by BA474.

Example 7: Nutrient Components Analysis

In order to confirm that the content of carbohydrates is reduced, the content of dietary fiber is increased, the content of crude proteins and essential free amino acids is increased to increase nutrient components and nutrient absorption rate in grain fermentation using BA245, a grain raw material, a BA245 fermented grains, a BA474 fermented grains and three enzyme foods fermented from commercially available grains [Secret of Fermented Enzyme produced by Daesang Wellife Co., Ltd., (hereinafter referred to as "DAESANG"); Seed fermented enzyme produced by LG Life Health (hereinafter referred to as "LG"); Fullvita Naemome Gain Enzyme Digest produced by ORGA Food (hereinafter referred to as "PULMUONE") were prepared and offered to the Korea Health Supplement Institute to conduct nutrient component analysis.

TABLE 5

| | | BA245 Fermented Grains (oat) | BA245 Fermented Grains (Quinoa) | BA245 Fermented Grains (Lentil) | BA245 Fermented Grains (Brown rice) | BA245 Fermented Grains (Sticky barley) | BA245 Fermented Grains (grain mixture of wheat germ and wheat bran) |
|---|---|---|---|---|---|---|---|
| Carbohydrate (% w/w) | | 70.12 | 72.49 | 61.67 | 79.57 | 76.05 | 58.55 |
| Crude protein (% w/w) | | 12.27 | 13.77 | 29.10 | 9.02 | 13.44 | 23.84 |
| Saccharide (mg/g) | | 44.78 | 18.99 | ND | 100.52 | 102.10 | ND |
| Essential | Threonine | 1.24 | 9.78 | 8.63 | 2.80 | 2.50 | 4.67 |
| Free | Lysine | 4.11 | 12.43 | 70.93 | 7.40 | 24.37 | 78.85 |
| Amino | Isoleucine | 1.05 | 7.77 | 9.87 | 5.56 | 7.74 | 16.95 |
| Acid | Leucine | 2.96 | 12.76 | 9.48 | 10.24 | 13.76 | 61.21 |
| (mg/100 g) | Methionine | 1.75 | 2.97 | 1.58 | 10.14 | 6.23 | 10.64 |
| | Phenylalanine | 12.20 | 12.52 | 68.76 | 27.96 | 63.37 | 109.41 |
| | Tryptophan | 5.98 | 6.03 | 5.78 | 5.63 | 18.15 | 89.63 |
| | Valine | 7.17 | 11.37 | 27.15 | 26.95 | 54.03 | 77.85 |
| | Total | 36.46 | 75.63 | 202.18 | 96.68 | 190.15 | 449.21 |

ND: Non-detectable

TABLE 6

| | | The grain Material (Entire The grain Mixture) | BA245 Fermented Grains | BA474 Fermented Grains | DAESANG | LG | PULMUONE |
|---|---|---|---|---|---|---|---|
| Carbohydrate (% w/w) | | 62.16 | 57.21 | 61.71 | 64.62 | 69.05 | 71.36 |
| Dietary fiber (% w/w) | | 23.37 | 27.32 | 23.52 | 9.67 | 7.75 | 12.74 |
| Crude protein (% w/w) | | 18.00 | 23.97 | 18.38 | 18.68 | 21.02 | 14.16 |
| Saccharide (mg/g) | | 32.87 | ND | 43.34 | 116.70 | 164.91 | 155.16 |
| Essential | Threonine | 16.78 | 57.81 | 20.91 | 7.00 | 3.89 | 15.47 |
| Free | Lysine | 9.18 | 141.06 | 25.06 | 18.11 | 6.21 | 35.96 |
| Amino | Isoleucine | 3.40 | 96.67 | 13.23 | 4.35 | 3.57 | 8.75 |
| Acid | Leucine | 4.16 | 192.30 | 60.73 | 39.43 | 5.06 | 24.89 |
| (mg/100 g) | Methionine | 1.31 | 45.44 | 9.48 | 6.92 | ND | 4.11 |
| | Phenylalanine | 4.54 | 206.15 | 56.39 | 35.75 | 4.98 | 15.45 |
| | Tryptophan | 29.44 | 78.09 | 33.01 | 9.79 | ND | 5.78 |
| | Valine | 6.79 | 211.79 | 65.30 | 7.88 | 5.64 | 14.40 |
| | Total | 75.60 | 1029.31 | 284.11 | 129.23 | 29.35 | 124.81 |

ND: Non-detectable

As a result, in Tables 5 and 6, it could be seen that the fermented grains produced using BA245 possessed enhanced nutrient components as compared with the raw materials in view of the reduced content of carbohydrates and saccharides, the increased content of dietary fibers, crude proteins and essential free amino acids, and the like, and that the BA245 fermented grains and the BA245 fermented grains (grain mixture of wheat germ and wheat bran) were superior to the BA474 fermented grains and other enzyme foods in view of the nutrient components.

Example 8: Analysis of Fibrinolytic Enzyme Activity

In order to determine whether the BA245 fermented grains have thrombolysis activity, fibrinolytic enzyme activity of the grain raw material and the BA245 fermented grains was measured. As control groups, plasmin (1 U/ml) and fermented soybean foods called 'Chungkukjang' (produced by Taekwang Co., Ltd.), Natto (produced by Pulmuone Co., Ltd., Azuma Co., Ltd., and Takano Co., Ltd.) and commercially available food (DAESANG; HI-SAENG produced by Hi-mo Natural Health Division), which are reported to have thrombolysis activity, were used.

After 1 g of a sample was mixed with 9 ml of a sterilized saline solution, the resulting solution was extracted using a stirrer (Wiseshaker, Daihan) at 4° C. for 30 minutes while mixing, followed by centrifugation (8,000×g, 4° C., 30 minutes) and filtering, and the resulting supernatant was used as an analysis sample.

8-1. Fibrin Plate Assay

To 10 ml of 2.4% completely dissolved fibrin solution (pH 7.0), 10 ml of 1.5% agarose solution was added and mixed, directly poured into a petri dish, and left at room temperature for 2 to 3 days until gel could be completely hardened, thereby obtaining a fibrin plate. The prepared fibrin plate was punched such that openings having a diameter of 4.5 mm were consistently formed, and to the openings, 20 μl of an analysis sample was added dropwise, and cultured at 37° C. for 24 hours. In order to clearly observe the size of transparent circles formed, 0.11M of trichloroacetic trichloroaceticacid was poured onto the fibrin gel.

As a result, the BA245 fermented grains exhibited thrombolytic activity of 220% higher than plasmin, 177% higher than Chungkukjang, 122% higher than Natto (PULMUONE), 117% higher than Natto (TAKANO) and 131% higher than Natto (AZUMA), 119% higher than enzyme food (DAESANG), and 142% higher than enzyme food (HI-SAENG) (Table 7 and FIG. 5).

TABLE 7

| Sample | Dissolve zone (mm) |
| --- | --- |
| Control group (Plasmin) | 8.6 |
| Grain raw material | — |
| BA245 fermented grains | 19.0 |
| Enzyme food (DAESANG) | 15.9 |
| Enzyme food (HI-SAENG) | 13.4 |
| Natto (PULMUONE) | 15.6 |
| Natto (TAKANO) | 16.3 |
| Natto (AZUMA) | 14.5 |
| Chungkukjang powder (TAEKWANG) | 10.7 |

8-2. Analysis of Fibrinolytic Activity

To 0.1 ml of the sample prepared in Example 8, 0.3 ml of 0.1M Tris-HCl buffer (pH 7.8) containing 10 mM calcium chloride was added, and warmed in a thermostat water bath at 30° C. for 5 minutes. To this solution, 0.3 ml of 1.2% fibrin solution (pH 7.8) was added, mixed, and left at 30° C. for 10 minutes, followed by adding 0.6 ml of 0.11 M trichloroacetic acid to the mixture in order to inhibit enzyme reaction. The resulting solution was used as a test solution. Separately, 0.3 ml of 0.1M Tris-HCl buffer (pH 7.8) was added to 0.1 ml of the sample and left in a thermostat water bath at 30° C. for 10 minutes, followed by adding 0.6 ml of 0.11 M trichloroacetic acid thereto. To the resulting solution, 0.3 ml of 1.2% fibrin solution (pH 7.8) was added, and the resulting solution was used as a blank test solution. Each of the test solution and the blank test solution was centrifuged at 12,000 rpm for 5 minutes, and a supernatant was collected and subjected to absorbance measurement at 275 nm for quantitative comparison of fibrinolytic enzyme activity.

As a result, it could be seen that the BA245 fermented grains exhibited the highest fibrinolytic activity and much better fibrinolytic activity than Natto (Table 8 and FIG. 6).

TABLE 8

| Sample | Fibrinolytic activity (FU/g) |
| --- | --- |
| The grain raw material | 19.86 |
| BA245 fermented grains | 136.17 |
| Enzyme food (DAESANG) | 53.90 |
| Enzyme food (HI-SAENG) | 25.53 |
| Natto (PULMUONE) | 68.06 |
| Natto (TAKANO) | 52.48 |
| Natto (AZUMA) | 36.88 |
| Chungkukjang powder (TAEKWANG) | 22.7 |

8-3. Fibrinolytic Activity Analysis of Strain BA245

In order to analyze fibrinolytic activity of the strain, the strain BA245 was compared with three strains isolated from commercially available Natto.

As a result, as shown in Table 9, it could be seen that the strain BA245 exhibited much better thrombolytic enzyme activity than the strains isolated from commercially available Natto.

TABLE 9

| Sample | Fibrinolytic activity (FU/g) |
| --- | --- |
| Strain BA245 | 1617 |
| Strain isolated from Natto (PULMUONE) | 1209 |
| Strain isolated from Natto (TAKANO) | 1072 |
| Strain isolated from Natto (AZUMA) | 1098 |

Example 9: Evaluation of Solid Meal Gastric Emptying Improvement by Feeding BA245 Fermented Grains 8-week old male SD (Sprague-Dawley) rats were allotted to experiment groups each consisting of ten rats, wherein all animals were acclimated to experimental diet and circumstance for one week. After acclimation, rats were fasted for 20 hours while freely drinking water in order to measure gastric emptying ability.

Experimental Example 1 was performed to evaluate gastric emptying per same hours under the condition that the same solid meal was fed. Specifically, on the day of experiment, 3 g of an experimental diet prepared by suspending 50% of barium sulfate, 0.6% of agarose, feed (AIN-93, Dyets) in water was orally administered to SD rats. Experiment was performed for a total of three experimental groups, wherein 15% of feed was added to a control group, while the diet formulated with 5% of the grain raw materials+10% of feed or formulated with 5% of BA245 fermented grains+10% of feed was fed to the experimental groups such that the fed amount could be the same. 40 minutes after administration, the stomach was excised and gastric emptying (%) was evaluated by measuring the weight of food remaining in the stomach.

Experimental Example 2 is a model in which an actual dose method in the human body is reflected, and improvement in gastric emptying when the same amount of feed was added and the BA245 fermented grains was further added was evaluated, in which the human equivalent dose corresponds to six times based on rat standard. 15% of feed was fed to the control group, and 600 mg/kg of the grain raw material and 600 mg/kg of the BA245 fermented grains were further fed to experimental groups. 40 minutes after administration, the stomach was excised and gastric emptying (%) was evaluated by measuring the weight of the diet remained in the stomach.

As a result, it could be seen that Experimental Example 1 exhibited significant increase in gastric emptying (p<0.05) as compared with the case where BA245 fermented grains or the grain raw material was administered (Table 10), and that Experimental Example 2 exhibited significant increase in gastric emptying (p<0.05) as compared with the case the grain raw material was fed (Table 11).

Gastric emptying is known to clinically decline in functional indigestion and it can be evaluated that digestion capability is enhanced when the BA245 fermented grains is digested together with food.

TABLE 10

| Experimental group | Gastric emptying (%, ±SD) |
|---|---|
| Feed (15%) | 23 ± 20 |
| Feed (10%) + Grain raw material (5%) | 9 ± 11 |
| Feed (10%) + BA245 fermented grains (5%) | 37 ± 21 |

TABLE 11

| Experimental group | Gastric emptying (%, ±SD) |
|---|---|
| Feed | 23 ± 20 |
| Feed + Grain raw material (600 mg/kg) | 9 ± 11 |
| Feed + BA245 fermented grains (600 mg/kg) | 37 ± 21 |

Example 10: Evaluation of Intestinal Permeation Improvement Through BA245 Fermented Grains Ingestion in an Acute Enteritis Animal Model An acute enteritis animal model was constructed by administering alcohol to rats, and the resulting rats were fed BA245 fermented grains with different intake concentrations to measure the degree of recovery in stomach function depending upon ingestion amount.

Animals used in experiment were 8-week old SD rats weighing 200 to 250 g, which were grown under 12 hours on/12 hours off light in a polycarbonate cage. After one week of acclimation, rats were treated in accordance with the following experiment design together with free diet.

Group 1: Control group

Group 2: Ethanol

Group 3: Ethanol+50 mg/kg/day of BA245 fermented grains

Group 4: Ethanol+100 mg/kg/day of BA245 fermented grains

Group 5: Ethanol+150 mg/kg/day of BA245 fermented grains

Group 6: Ethanol+100 mg/kg/day of grain raw material

Alcohol was orally administered to Groups 2 to 6 for four weeks to induce irritable bowel syndrome, thereby causing reduction in intestinal function. An initial dose was 2 g/kg/day. The amount of alcohol to be orally administered was increased weekly by 1 g/kg/day, and by the time of the fourth and final week, 5 g/kg/day was orally administered. After four weeks, intestinal permeation ability was measured.

Specifically, intestinal permeation ability was determined by sacrificing rats, isolating the ileum, and soaking the isolated ileum in Krebs-Henseleit bicarbonate buffer (KHBB: bicarbonate buffer), followed by suturing one end of the ileum, and injecting 100 μl of FITC-dextran into the lumen. The other end of the intestine was sutured to form 8 cm of a gut sac. The gut sac was washed with KHBB, followed by putting in 2 mL of KHBB and incubating at 37° C. for 20 minutes. FD-4 of FTTC-dextran passed from the lumen to incubation buffer was measured at 530 nm using a spectrophotometer. Permeability of FD-4 is represented in μg at 1 cm per minute.

As a result, it could be seen that there was significant reduction in intestinal permeability due to alcohol administration by feeding the BA245 fermented grains, and particularly, it could be seen that the group administered 100 mg or more per kg of body weight exhibited recovery close to the normal group (FIG. 7).

Example 11: Analysis of Serous Membrane Enhancement by BA245 Fermented Grains Intake Through an Acute Enteritis Animal Model If serous fluid comes to leak due to serous membrane weakening, serous inflammation can be induced, and in order to quantitatively measure recovery of intestinal permeability increased due to alcohol, analysis of tight junction proteins of intestinal cells participating in intestinal permeability was performed using the animal model designed in Example 10. Representative main tight junction proteins participating in cellular bonding of serous membranes are ZO-1, claudin, and occludin, wherein the expression degree of genes corresponding to each protein was measured through RT-PCR analysis, and the bonding degree between intestinal cells was identified, thereby confirming effects of fermented grains intake. In RNA extraction, TRIzol was utilized and concentration thereof was measured using a NanoDrop spectrophotometer.

As a result, it could be seen that expression of claudin and occludin was increased in proportion to BA245 fermented grains administration and feeding concentration, thereby enhancing the serous membrane ($p<0.05$) (FIGS. 8A and 8B).

Example 12: Evaluation of Structural Damage Amelioration by BA245 Fermented Grains Intake Through Intestinal Histological Analysis Intestinal histological analysis was performed using an animal model designed in Example 10. Intestinal tissues sampled from each group were fixed in a 10% formalin solution, followed by dehydration using ethanol, and then fixed in paraffin. A 4 m thick section was dyed with hematozylin-Eosin and the dyed fragments were observed through a microscope.

It could be confirmed that crypt and villus structures of intestinal walls were broke down when intestinal injury was developed by alcohol, and it could be observed that the BA245 fermented grains intake group, particularly the group to which 100 mg or more of BA245 fermented grains per kg of body weight was fed, exhibited recovery close to normal tissues (FIG. 9).

Example 13: Measurement of Antioxidant Activity of BA245 Fermented Grains

Antioxidant activity is known to control various kinds of disease caused by oxidative stress (lipid and oxide accumulation prevention, enzyme inactivation, cell aging, arteriosclerosis, diabetes, stroke, cancer, DNA synthesis decline, adult diseases and aging, and the like). A grain raw material, a BA245 fermented grains, and two kinds of commercially available enzyme food (DAESANG and HI-SAENG) were compared.

Specifically, samples and 70% ethanol were mixed in a ratio of 1:9, followed by extracting while stirring at 30° C. for 3 hours using a stirrer (Wiseshaker, Daihan). The resulting mixture was centrifuged at 8,000×g at 4° C. for 10 minutes, followed by collecting the supernatant, which was subjected to identical extraction, and the finally collected supernatant was filtered. The filtered supernatant was dried using a freeze dryer until solvents could be completely removed, and the resulting mass was utilized as an analysis sample.

10 mg of the sample was completely dissolved in 1 ml of 70% ethanol to prepare a test solution. 38.5 mg of ABTS and 6.6 mg of potassium persulfate were dissolved in 5 ml of distilled water, followed by stirring, and then were left under dark conditions for 12 to 16 hours to generate radicals. Thereafter, an ABTS solution was prepared so as to have an absorbance at 734 nm of 0.7±0.02.

To 10 μl of the test solution, 990 μl of the ABTS solution was added, mixed, and left in a dark room for 10 minutes, followed by measuring absorbance at 734 nm. All experiments were repeated three times or more, and then mean values and standard deviation values thereof were calculated.

As a result, it could be seen that free radical scavenging ability of the BA245 fermented grains was 43.7%, which was much higher than those of the grain raw material and commercially available enzyme foods (FIG. 10). Through this experiment, it was also confirmed that antioxidant activity could be increased by fermentation using BA245 and was much higher than those of conventional two enzyme foods.

The invention claimed is:

1. A bacterial composition, comprising:
a strain of *Bacillus amyloliquefaciens* BA245 deposited under accession number KCTC12905BP;
wherein the bacterial composition is a powdered and freeze-dried composition.

2. Fermented grains produced with a strain of *Bacillus amyloliquefaciens* BA245 deposited under accession number KCTC 12905BP.

3. A method of producing fermented grains according to claim 2, comprising:
(a) inoculating a grain with the strain of *Bacillus amyloliquefaciens* BA245 deposited under accession number KCTC 12905BP; and
(b) culturing the strain to obtain fermented grains.

4. The method of producing the fermented grains according to claim 3, wherein, in step (a), the grain comprises at least one grain selected from the group consisting of wheat, wheat germ, wheat bran, white rice, brown rice, germinated brown rice, barley, oats, red rice, sticky black rice, sticky rice, rice bran, soybeans, black soybean, black beans, quinoa, lentils, and adlay.

5. The method of producing the fermented grains according to claim 3, wherein, in step (a), the grain comprises wheat germ and wheat bran.

6. The method of producing the fermented grains according to claim 5, wherein the wheat germ and the wheat bran are present in an amount of 40 parts by weight to 100 parts by weight relative to 100 parts by weight of the grain in step (a).

7. The method of producing the fermented grains according to claim 5, wherein, in step (a), the grain further comprises at least one grain selected from the group consisting of oats, lentils, brown rice, sticky barley, and quinoa.

8. The method of producing the fermented grains according to claim 3, wherein, in step (a), the grain has a moisture content of 30% (v/w) to 70% (v/w).

9. The method of producing the fermented grains according to claim 3, further comprising: treating the grain with moisture prior to step (a).

10. The method of producing the fermented grains according to claim 3, further comprising: performing heat treatment of the grain prior to step (a).

11. The method of producing the fermented grains according to claim 3, further comprising: performing heat treatment after treating the grain with moisture prior to step (a).

12. The method of producing the fermented grains according to claim 3, wherein culturing in step (b) is solid culturing.

13. The method of producing the fermented grains according to claim 3, wherein culturing in step (b) is performed at a temperature of 20° C. to 50° C.

14. The fermented grains according to claim 2, wherein the fermented grains are produced by a method producing fermented grains, comprising:
(a) inoculating a grain with the strain of *Bacillus amyloliquefaciens* BA245 deposited under accession number KCTC 12905BP; and
(b) culturing the strain to obtain the fermented grains.

15. A food composition comprising a strain of *Bacillus amyloliquefaciens* BA245 deposited under accession number KCTC12905BP or fermented grains comprising the strain of *Bacillus amyloliquefaciens* BA245 deposited under accession number KCTC 12905BP.

16. The food composition according to claim 15, wherein the food composition is an enzyme food.

17. A composition for thrombolysis comprising: a strain of *Bacillus amyloliquefaciens* BA245 deposited under accession number KCTC12905BP or fermented grains comprising the strain of *Bacillus amyloliquefaciens* BA245 deposited under accession number KCTC 12905BP.

18. The composition for thrombolysis according to claim 17, wherein the composition for thrombolysis is a composition for prophylaxis, amelioration or treatment of myocardial infarction, venous thrombosis, stroke, cerebral infarction, cerebral thrombosis, or cerebral embolism.

19. A composition for digestion improvement, comprising: a strain of *Bacillus amyloliquefaciens* BA245 deposited under accession number KCTC12905BP or fermented grains comprising the strain of *Bacillus amyloliquefaciens* BA245 deposited under accession number KCTC 12905BP.

20. A composition for prophylaxis, amelioration or treatment of bowel inflammation, serous membrane weakening or intestinal injury, comprising: a strain of *Bacillus amyloliquefaciens* BA245 deposited under accession number KCTC12905BP or fermented grains comprising the strain of *Bacillus amyloliquefaciens* BA245 deposited under accession number KCTC 12905BP.

21. A composition for antioxidation comprising: a strain of *Bacillus amyloliquefaciens* BA245 deposited under accession number KCTC12905BP or fermented grains comprising the strain of *Bacillus amyloliquefaciens* BA245 deposited under accession number KCTC 12905BP.

22. A method for prophylaxis, amelioration or treatment of myocardial infarction, venous thrombosis, stroke, cerebral infarction, cerebral thrombosis, or cerebral embolism, comprising administration of the fermented grains according to claim 2 to a subject in need thereof.

23. A method for improving digestive function of a subject, comprising administration of the fermented grains according to claim 2 to a subject in need thereof.

24. A method for prophylaxis, amelioration or treatment of bowel inflammation, serous membrane weakening or intestinal injury, comprising administration of the fermented grains according to claim 2 to a subject in need thereof.

25. A method for reducing active oxygen in a subject, comprising administration of the fermented grains according to claim 2 to a subject in need thereof.

26. A bacterial composition comprising:
a pre-cultured strain of *Bacillus amyloliquefaciens* BA245 deposited under accession number KCTC12905BP in a number of the bacteria of $1 \times 10^5$ CFU/g to $1 \times 10^{10}$ CFU/g;
and a culture medium for the bacteria.

* * * * *